United States Patent [19]
Friedman et al.

[11] 3,990,850
[45] Nov. 9, 1976

[54] DIAGNOSTIC TEST CARD

[75] Inventors: Stephen B. Friedman, Claremont; Mel J. Riley, Covina, both of Calif.

[73] Assignee: Akzona Incorporated, Asheville, N.C.

[22] Filed: Jan. 6, 1976

[21] Appl. No.: 646,830

[52] U.S. Cl. .......................... 23/230 B; 23/253 TP; 128/2 F; 424/11; 424/12
[51] Int. Cl.² .................. G01N 31/00; G01N 33/16
[58] Field of Search .................. 23/230 B, 253 TP; 424/11, 12; 206/484, 216, 528, 538; 195/103.5, 127

[56] References Cited
UNITED STATES PATENTS

| | | | |
|---|---|---|---|
| 2,304,817 | 12/1942 | Grozin | 424/12 X |
| 2,770,572 | 11/1956 | Eldon | 23/230 R UX |
| 3,074,853 | 1/1963 | Brewer | 424/12 |
| 3,502,437 | 3/1970 | Mass | 23/230 B X |
| 3,666,421 | 5/1972 | Price | 23/230 B X |
| 3,770,383 | 11/1973 | Price | 424/12 X |
| 3,838,012 | 9/1974 | Higgens et al. | 23/253 TP X |

*Primary Examiner*—Robert M. Reese
*Attorney, Agent, or Firm*—Francis W. Young

[57] ABSTRACT

A novel test card adapted for the performance of an immunochemical, diagnostic or serological test upon its surface, and which is provided with an end flap which may be folded over to enclose and preserve the test results. The flap portion is provided with circular openings which when folded over, are in registry with circular test areas on the surface of the card, permitting visual observation of the test results. The card may be used, for example, for blood group typing.

9 Claims, 3 Drawing Figures

DIAGNOSTIC TEST CARD

BACKGROUND OF THE INVENTION

The present invention relates to a novel test card adapted for the performance of an immunochemical, diagnostic, or serological test upon its surface and provided with means for preserving and permitting observation of the test results.

In U.S. Pat. Nos. 3,666,421 and 3,770,383, there are disclosed single test slides or cards having on the surface thereof all the necessary reagents for performing an immunochemical, diagnostic, or serological test in the form of a demarcated circumscribed test area within which are deposited one or more solid dried aqueous test reagents. These deposits upon being moistened, are reconstituted to the respective test reagents with the liquid to be tested, and then form a spot of reaction mixture. Thus the test can be performed in situ and the card kept for record purposes. In one embodiment the test slide of these patents may be enclosed by a separate cover member of thin embossed transparent plastic material bonded to a metal foil or foil laminate, the cover being intended to protect the test slide enclosed therein prior to use, and hence being removable.

In U.S. Pat. No. 2,770,572 there is described a blood grouping card comprising a supporting sheet upon which test sera are carried in a dry state until use, and upon which test reaction mixture dries and remains as a deposit test record. This has the drawback that the test deposits remain unprotected and may rub off or otherwise be damaged in storage or filing.

In U.S. Pat. No. 3,074,853 there is disclosed a serological test card having deposited thereon a test reagent and an absorbent in a circular shape, but no cover is provided for the test results.

In U.S. Pat. No. 3,502,437 there is described a blood group identification card having two cavities in the body of the card comprising a hole in the card, one side of which is covered by a backing member of transparent material affixed to the underside of the card, which cavity is used to contain test material, such as blood serum and cells, the card having a transparent protective coating applied to its upper surface to seal in the test materials. This necessitates the coating application as a separate operation.

U.S. Pat. No. 3,838,012 describes a test paper having a plurality of circumscribed predetermined areas printed on its surface, the test paper being absorbent and made of filter paper. The printed areas are circular, the circle acting as a barrier to retain a liquid test sample. The test paper can be stored, but no cover for the test portions is proposed.

GENERAL DESCRIPTION OF THE INVENTION

In accordance with the present invention, there is provided a novel test card adapted for the performance of an immunological diagnostic, or serological test upon its surface, and provided with means for preserving and permitting observation of the test results.

In accordance with a presently preferred embodiment, there is provided a test card for the performance and preservation of blood group tests, and the invention will be described with reference thereto. However, it is to be understood that the discussion in regard thereto is for purposes of illustration only, and that the test card of the invention is adapted for the performance of a wide variety of diagnostic and immunochemical tests, including those described in U.S. Pat. Nos. 3,666,421 and 3,770,383, such as, for example, human chorionic gonadotropin, rheumatoid factor, monoucleosis, and others.

The novel test card of the invention and the method of its use will be principally illustrated with respect to reagents for the determination of types A, B, AB and O blood groups.

The test card comprises a substantially plane strip of a substrate material having at least one test surface thereof which is substantially insoluble in, impermeable to, non-absorbent to, and wettable by, water, and carrying on its test surface at least one circumscribed test area containing at least one deposited dried aqueous reagent providing a predetermined amount of a test reagent, which upon being moistened with a liquid to be tested is reconstituted to the test reagent, and then united with a portion of liquid to be tested, forming an area of reaction mixture.

DESCRIPTION OF THE PREFERRED EMBODIMENT

The main body of the test card includes at least one end portion joined thereto along a fold line running transversally to said main body. Said end portion includes at least one opening provided with a transparent viewing member and forms a flap which is foldable along said fold line so that when folded over onto the face of the test card, said opening is in registry with said circumscribed test area, to permit the viewing of the contents, and subsequent sealing thereof, for purposes of preservation and filing of the test card.

The nature and method of preparation and use of the test cards of the invention will be better understood by reference to the accompanying drawings, which illustrate a presently preferred embodiment, but are not to be considered as limiting the invention thereto. In the drawings.

Figure 1:
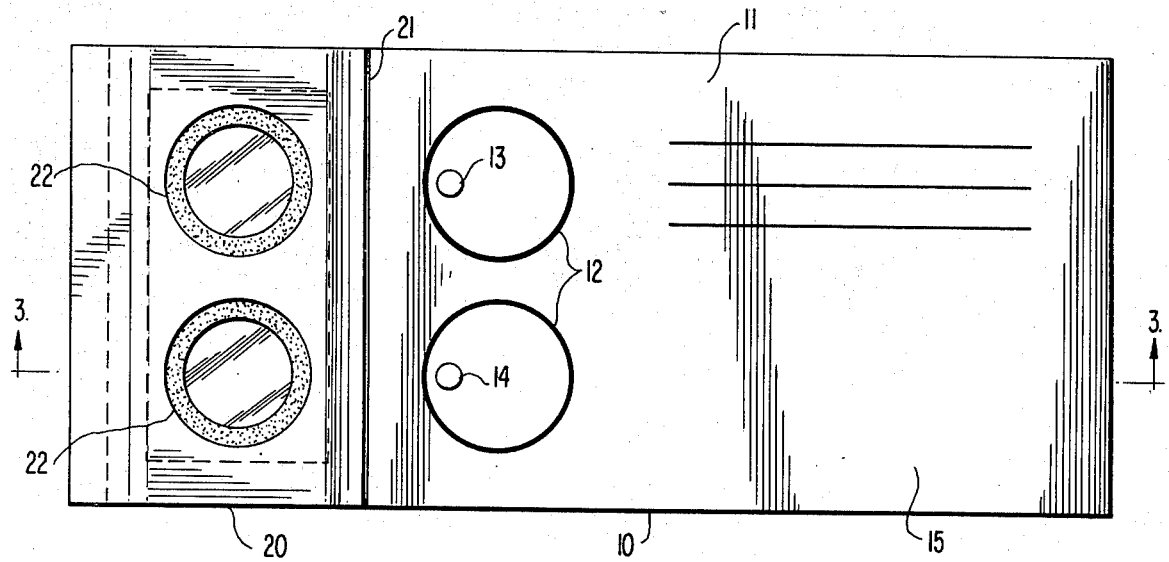
FIG. 1 is a plan view of the upper surface of a test card and attached end portion, the card having thereon two circumscribed areas containing, respectively, dried blood group antisera test spots.

Referring now to the drawings, FIG. 1 shows a test card suited for the performance of a blood typing test for types A, B, AB or O. The card 10 comprises a substantially rectangular sheet or strip of substrate material 11 having the impermeability toward water and the wettability referred to previously. While the substrate material may be glass, glazed porcelain, or a synthetic plastic treated to make it wettable, to which the end portion is attached by a suitable hinge, it is advantageously made of a paper product such as cardboard.

In the embodiment shown in FIG. 1, the substrate is a thin sheet of cardboard having one or both surfaces coated with a coating 15 of a water-impermeable and water-wettable coating of plasticized nitrocellulose, having a thickness which will maintain the flexibility of the cardboard, e.g. about 0.02 inch. In all cases, the surface of the card which carries the test reagent areas should be water-insoluble.

The main body of the test card 10 bears on its coated surface two circles 12 of contrasting color to the surface, which serves to demarcate the location of the area containing the test reagent. These demarcations are shown as circles, however, but may be of any desired shape, e.g. rectangular, with matching shape of the flap opening. In the embodiment shown in FIG. 1, there are two test reagents. The first of these, designated 13, is a solid dried spot of antiserum A, which when mixed with the blood of a person having the type of blood in Group A, will agglutinate, thus identifying the test blood sample. There is also, designated 14, a solid dried spot of antiserum B, which will similarly identify the blood of a person belonging in blood Group B.

The main body of the test card 10 may conveniently be of a size suitable for filing when the end flap is turned thereon, for example, 3 × 5 inches. The test reagent spots advantageously have an average diameter between about 5 and about 15 mm. so that they may be wetted within the test area by the liquid to be tested, or by added water, when these are applied to the card.

Joined to the main body 11 of the test card 10 is an end or flap portion 20, being attached along line 21. The attachment may be by a suitable hinge (not shown), but preferably, in the embodiment shown, the flap portion is integral with the main body of the card, forming a continuation thereof, and is capable of being folded over onto the test face of the card along a fold line 21, which may be slightly scored into the card surface, to aid in the folding, said fold line running transversely to the long edge of the main body, as shown.

Figure 2:
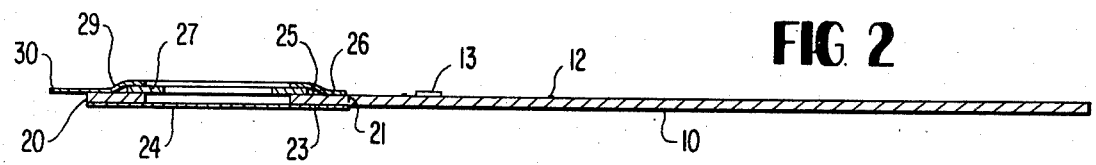
FIG. 2 is a cross-sectional view of the test card of FIG. 1, taken along the line 3 — 3.
Figure 3:
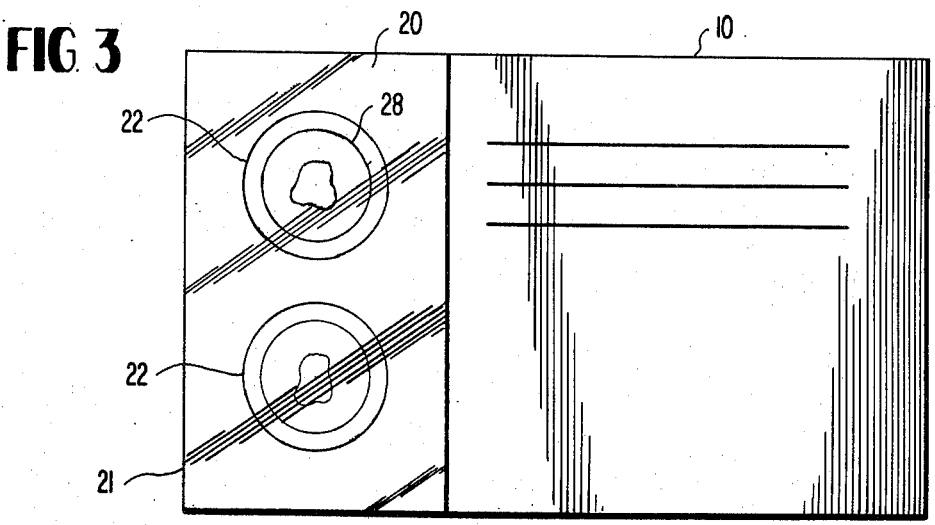
FIG. 3 is a plan view of the test card of FIG. 1 with the end portion folded over onto the test surface with test results visible therethrough.

Said flap portion 20, shown in open position in FIG. 1 and in cross-section in FIG. 2, is provided with circular openings 22, which are spaced apart from said fold line 21, a distance such that, when the flap portion 20 is folded over onto the main body of the card, the openings 22 will be in registry with the corresponding circular test areas 12, exposing the contents of the latter to view through the openings 22.

There is bonded to the lower side 23 of flap member 20 a layer of transparent sheet or film material 24, which may be of cellophane, polyethylene, or other suitable plastic material, which is coextensive with the entire surface of the flap, and which when the flap is folded over onto the main body of the test card, permits viewing of the test materials. The obverse side 25 of the flap, i.e. the side forming an extension of the test card surface, is coated with a layer 26 of adhesive material, namely a pressure-sensitive adhesive of any suitable type, upon which there is mounted a thin layer 27 of an absorbent paper, such as blotting paper, which is rectangular in shape, with its edges spaced away from the edges of the flap portion. This absorbent paper layer has therein a pair of circular openings 28 of a slightly smaller diameter than the diameter of the openings 22, and is intended to prevent contact of the flap bottom layer with the test reagents on the main body of the card, when the flap is folded over, acting as a sort of washer, and also to absorb excess reagent.

Extending across the upper face 25 of the flap member is a layer of peelable or strippable paper 29 which has a portion 30 which extends beyond the outer edge of the flap to permit grasping of the strippable for removal. The peelable member 30 is provided with a suitable adhesive permitting stripping, of any conventional type. When the test is completed, the peelable member is removed exposing the adhesive layer 26, which when the flap is folded over, serves to seal the test area of the test card.

The manner of using the test card of the invention will be illustrated with respect to the performance of a blood group test, but this is not to be considered as limiting the invention thereto.

The test card is first prepared with test reagent 13 being a solid dried spot of antiserum of blood group A, and reagent 14 being a solid dried spot of antiserum of blood group B. The preparation of these sera is well known and can be carried out, for example, as described in U.S. Pat. No. 2,770,572.

The test card with the reagents in the respective circles on the surface facing the user, is placed horizontally so that the flap portion is open and the card fully expanded, with the strippable backing on the flap portion closest to the user. The absorbent paper member 27 may be of a contrasting color, or may be shaped in the form of an A and B, instead of circles, to aid in A-B-O blood group interpretation.

With the test card in the aforementioned position, one drop of distilled water (approximately 0.03 ml) is placed on top of each spot of test antiserum, to reconstitute the reagents. Then a volume of blood to be tested equal to approximately ¼ to ½ of the distilled water volume applied previously, is placed next to each reagent spot, viz. the anti-A-serum and anti-B-serum. The first reagent is reconstituted by stirring the water into it with a stirrer, e.g. a toothpick until thoroughly mixed. Then a blood sample is stirred into the reconstituted reagent using a fresh stirrer, and the reaction mixture is spread to cover the entire area of the circumscribed test area. Next the other spot B is reconstituted with water and mixed with blood to be tested in the same manner as spot A, using fresh stirrers. Thereafter the test card is rocked gently for about 2 minutes, at the end of which time the reactions on the card may be interpreted.

If agglutination takes place in test area A, the blood sample is type A. If agglutination takes place in area B, the blood sample is type B. If agglutination takes place in both test areas, the blood is type AB. If no agglutination occurs, the blood is type O.

At the end of two minutes, the card is placed on a flat surface, the strippable paper on the surface of the flap is removed, and the flap folded over. Pressure is applied to the adhesive covered areas around the holes cut in the flap portion. The card is lifted off the flat surface and gently rocked to bring the reaction mixture into contact with the absorbent paper.

The foregoing procedure results in a closed, covered system within which the test results are sealed and may be preserved and filed, and are protected from environmental injury. The portion of the test card apart from the circles may be used to record additional information, and thus the entire card is adapted for storage in a standard filing system. If desired the portion of the test card not covered by the flap can be raised so that when the flap is folded over the surface of the card is flat. Moreover, a small hole, covered by a transparent material, may be placed within the area for the reaction mixture, thus providing a light path through the entire card. This can lend itself to a detection device for agglutination, using a light source which penetrates the reaction mixture. This enables coupling to a printer, whereby the reaction can be interpreted and the type printed on the test card.

What is claimed is:

1. A test card for performing immunochemical, diagnostic, or serological tests on the surface thereof, comprising:
   a. a substantially plane strip of a substrate material having at least one test surface thereof which is substantially insoluble in, impermeable to, nonabsorbent to, and wettable by water, and including a main body and a foldable end portion joined to said main body along a fold line;
   b. said main body having on said test surface at least one circumscribed test area containing at least one deposited dried aqueous reagent providing a predetermined amount of a test reagent, which upon being moistened is reconstituted to said test reagent;
   c. said end portion forming a flap provided with at lease one opening positioned in such manner that when said flap is folded over onto said main body, said opening is in registry with said test area, permitting viewing of the test area contents.

2. The test card of claim 1 in which said test areas are circular in configuration.

3. The test card of claim 1 in which said openings in said flap portion are circular in configuration and of approximately the diameter of test areas on said main body which are also circular in configuration.

4. The test card of claim 1 in which there are two test areas on the main body, each enclosing a dried spot of blood type antiserum test reagent.

5. The test card of claim 1 in which said flap is integral with the main body of the test card.

6. The test card of claim 1 in which said flap portion has bonded to the lower side thereof a transparent sheet layer to permit viewing of the test results when the flap is folded over onto the main body of the card.

7. The test card of claim 1 in which the upper surface of said flap portion is coated with a layer of an adhesive material.

8. The test card of claim 1 in which said flap portion has mounted on the upper surface a layer of an absorbent sheet provided with circular openings of slightly smaller diameter and in registry with the corresponding openings in said flap portion.

9. The test card of claim 1 in which said flap portion is further provided with a layer of strippable material extending over and slightly beyond the outer edge of the upper surface thereof, which is removable to expose an adhesive layer on said flap surface.

* * * * *